(12) United States Patent
Tripp et al.

(10) Patent No.: US 8,409,240 B2
(45) Date of Patent: Apr. 2, 2013

(54) EMBOLIC PROTECTION DEVICE

(75) Inventors: Grace Tripp, Chanhassen, MN (US); James Anderson, Fridley, MN (US); Michele Zoromski, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 427 days.

(21) Appl. No.: 12/626,089

(22) Filed: Nov. 25, 2009

(65) Prior Publication Data

US 2011/0125180 A1    May 26, 2011

(51) Int. Cl.
*A61M 29/00* (2006.01)
(52) U.S. Cl. .................................................. 606/200
(58) Field of Classification Search .............. 606/200, 606/108, 110, 113, 198; 623/1.11, 1.12, 623/1.35
See application file for complete search history.

(56) References Cited

U.S. PATENT DOCUMENTS

| | | | |
|---|---|---|---|
| 5,683,451 A * | 11/1997 | Lenker et al. ............. | 623/1.11 |
| 6,019,787 A | 2/2000 | Richard et al. | |
| 6,168,617 B1 | 1/2001 | Blaeser et al. | |
| 6,346,116 B1 * | 2/2002 | Brooks et al. ............. | 606/200 |
| 6,350,278 B1 * | 2/2002 | Lenker et al. ............. | 623/1.12 |
| 6,514,280 B1 * | 2/2003 | Gilson ...................... | 623/1.11 |
| 6,607,552 B1 | 8/2003 | Hanson | |
| 6,626,934 B2 | 9/2003 | Blaeser et al. | |
| 6,878,153 B2 | 4/2005 | Linder et al. | |
| 6,945,990 B2 * | 9/2005 | Greenan ................... | 623/1.12 |
| 6,951,570 B2 | 10/2005 | Linder et al. | |
| 6,962,598 B2 | 11/2005 | Linder et al. | |
| 6,997,939 B2 | 2/2006 | Linder et al. | |
| 7,306,575 B2 | 12/2007 | Barbut et al. | |
| 7,344,551 B2 | 3/2008 | Barbut et al. | |
| 7,857,826 B2 * | 12/2010 | Eskuri et al. ............. | 606/200 |
| 2002/0026211 A1 * | 2/2002 | Khosravi et al. .......... | 606/200 |
| 2002/0099436 A1 | 7/2002 | Thornton et al. | |
| 2005/0096692 A1 | 5/2005 | Linder et al. | |
| 2005/0283185 A1 | 12/2005 | Linder et al. | |
| 2006/0089666 A1 | 4/2006 | Linder et al. | |
| 2007/0233179 A1 * | 10/2007 | Brady et al. .............. | 606/200 |

* cited by examiner

*Primary Examiner* — Elizabeth Houston

(74) *Attorney, Agent, or Firm* — Seager, Tufte & Wickhem LLC

(57) ABSTRACT

The disclosure relates to an embolic filter, a support structure therefor, and methods for maintaining said filter in a compact state prior to deploying the filter.

5 Claims, 7 Drawing Sheets

EMBOLIC PROTECTION DEVICE

TECHNICAL FIELD

This disclosure relates generally to embolic filters, support structures therefor, and methods for deploying said filters.

BACKGROUND

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

Such percutaneous interventional procedures, i.e., angioplasty, atherectomy, and stenting, can dislodge material from the vessel walls. This dislodged material can enter the bloodstream. Some existing devices and technology use a filter for capturing the dislodged material from the bloodstream. Such filters are deployed downstream of the blockage and commonly are passed by or through the blockage prior to the percutaneous interventional procedures. Accordingly, it is common to introduce the filter into the vessel in a folded or compacted form and to expand or deploy it once it has passed the blockage.

SUMMARY

This disclosure pertains to an embolic filter and method of deploying same. The filter includes an augmented constraint apparatus for delivery and deployment of the filter within a lumen, said apparatus comprising an elongated support member for an intraluminal filter, said support member having a proximal end, a distal end, and a shaft therebetween; an intraluminal filter associated with the distal end of the support element, said filter comprising a plurality of outwardly biased struts, said filter having a collapsed state and a deployed state; a motion restricting member disposed about at least a portion of the outwardly biased struts of the filter in the collapsed state; a containment structure having two or more apertures therein; and an activation element having a first position and a second position, wherein in the first position, the activation element engages the two or more apertures of the containment structure and the containment structure encompasses at least a portion of the outwardly biased struts, further wherein in the second position, the activation element is disengaged from at least one of the apertures of the containment structure allowing the intraluminal filter to move from the collapsed state toward the deployed state. The motion restricting member acts in cooperation with the containment structure to maintain the filter in a compact state until the containment structure is released, whereupon the motion restricting member moves as the filter deploys.

The disclosure also relates to a filter which includes an augmented constraint apparatus for delivery and deployment of the filter within a lumen comprising an intraluminal filter having a plurality of outwardly biased struts, a motion restricting member disposed about at least a portion of the outwardly biased struts, said motion restricting member providing an inward force insufficient to prevent expansion of the filter from a collapsed state to an expanded state, and a containment structure, wherein the containment structure encompassed at least a portion of the outwardly biased struts and, in combination with the motion restricting member, provides sufficient inward force to prevent expansion of the filter from a collapsed state to an expanded state until the containment structure is released or otherwise removed.

Further, the disclosure relates to a method of containing and deploying an intraluminal filter by providing the filter with an augmented constraint apparatus, collapsing the filter within the augmented constraint apparatus, delivering the contained filter to an appropriate portion of a lumen, removing or releasing a containment structure, allowing a motion restricting member to move from a first position to a second position thereby releasing the filter within the lumen.

DETAILED DESCRIPTION

Figure 1:
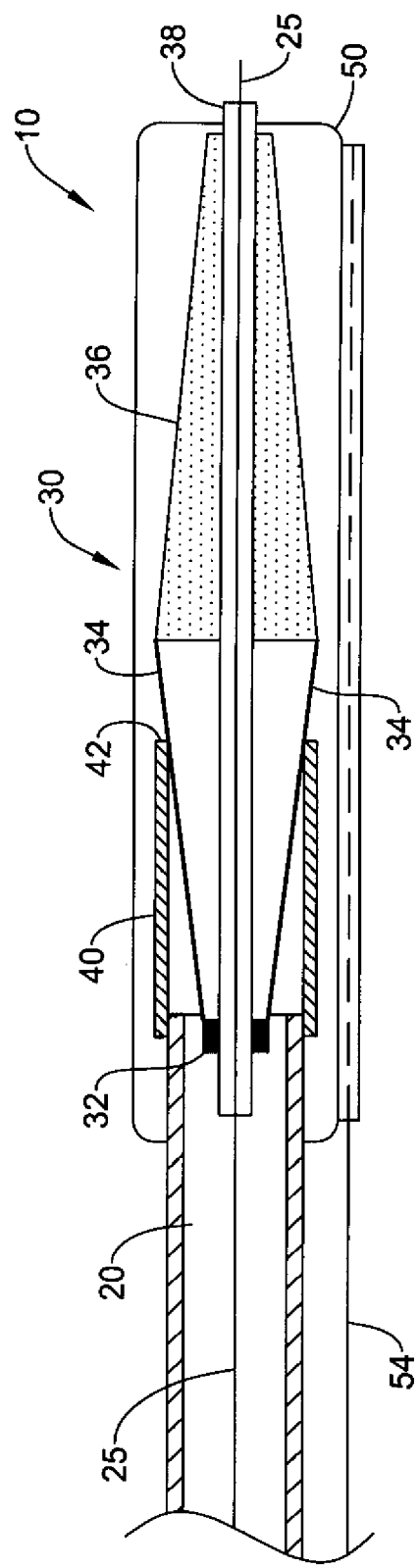
FIG. 1 is a cross-section view of an embolic filter in a collapsed state.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

The embolic filters disclosed herein include an elongated support member and may be advanced through a blood vessel along a catheter or guidewire until they are positioned downstream of an obstruction to be treated. The filters are then deployed in various ways, such as by releasing a containment structure within which they had been compressed. These filters include several structural elements such as struts which tend to bias a filter element consisting of a porous sheet or mesh in the form of a cone or basket toward expansion to completely span the lumen of the vessel to be protected. When the procedure has been completed, the filter is withdrawn by at least partially collapsing the filter and reintroducing the filter into a catheter or sheath to contain any captured emboli or other debris while the filter is withdrawn from the vessel.

Referring now to FIG. 1, filter and augmented constraint apparatus 10 comprises an elongated support member 20, often a catheter, which delivers filter 30 in an initially collapsed state. Filter 30 may include a filter membrane 36 supported, at least in part, by a plurality of struts 34 radiating outward from hub 32. The filter membrane 36 may include a plurality of openings sized to pass blood cells, but to retain emboli, thrombi, and other debris. In addition to the hub, struts and filter membrane, the filter may optionally include a spinner tube 38 which allows the filter limited translation and rotation about a deploying guidewire 25, catheter, or the like. Struts 34 are biased to expand outward to completely span the lumen of the vessel to be protected. During delivery, the struts 34 and filter membrane 36, if present, are folded and compressed to provide a minimal radial cross-sectional area as the filter is advanced past the blockage. Although this may be accomplished in many ways, at least part of the collapsed filter 30 may be surrounded by containment structure 50. Suitable containment structures 50 are known in the art. In some embodiments they wrap around the filter as a band, strip, loops, or the like provided with two or more apertures through which an activation element 54 may be passed to complete a containing structure. In other embodiments, they may be simple sheaths which may be released by withdrawal along the elongated support member until they no longer contain the struts. In the embodiment depicted, the containment structure 50 is in the form of a strip and the activation element 54 passes alternately through apertures along the opposed edges of the strip in the manner of a stitched seam to surround and compress the struts 34.

Although such containment structure 50 and activation element 54 pairs are often satisfactory to overcome the outward bias of the struts, the force associated with some filters in their collapsed state may create an undesirable bulge in the constraint apparatus 10. In addition, the outward force associated with the biased struts may make it difficult to apply the containment structure 50 in its minimal cross-section configuration. The addition of one or more motion restricting members 40 encircling the struts 34 along at least a portion of their length provides additional compressive force on the struts.

Figure 2:
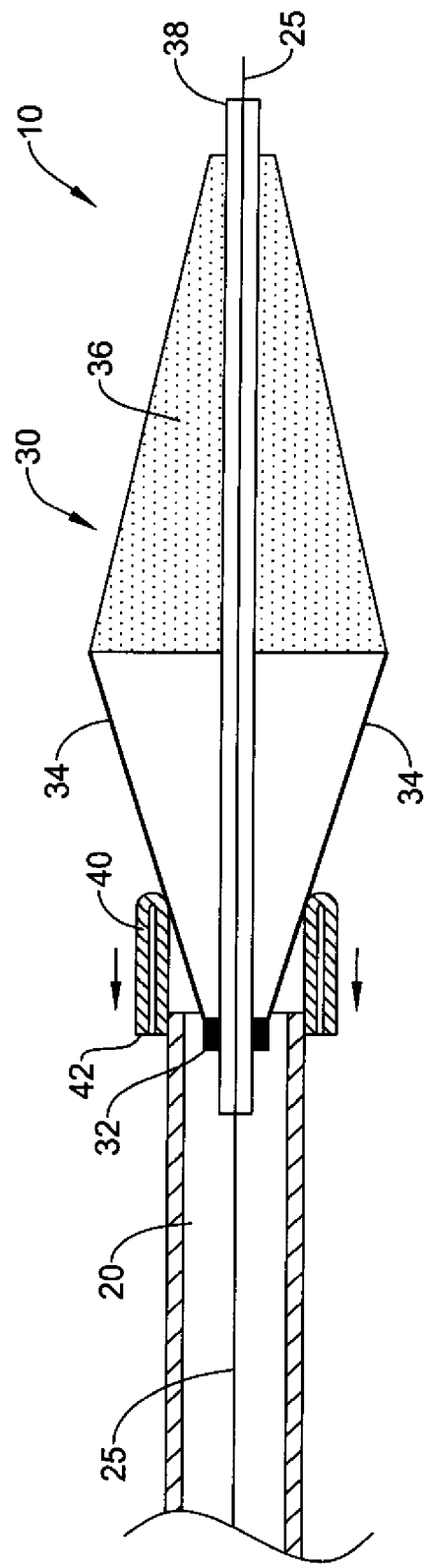
FIGS. 2 and 3 are cross-section views of the embolic filter of FIG. 1 as it deploys.
Figure 3:
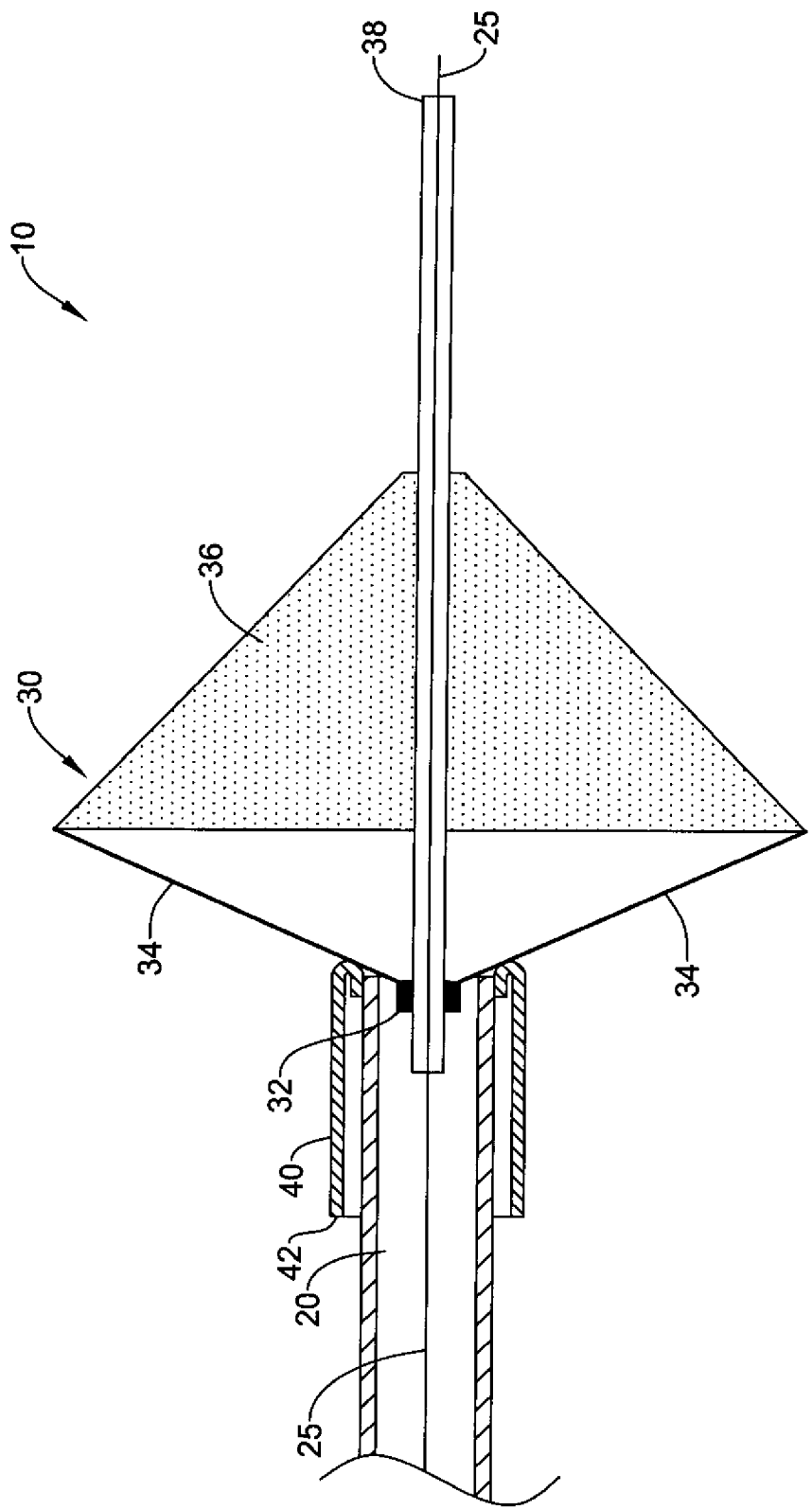

In the embodiment of FIGS. 1-3, a motion restricting member 40, in the form of an elastomeric tube, surrounds the struts 34 and a distal end of elongated support element 20. Following disengagement of the activation element 54 from one or more of the apertures associated with the containment structure 50 thereby releasing the filter 30, it is desirable that the struts 34 expand at least slightly to an intermediate state illustrated in FIG. 2. As the struts 34 separate, the forces on the motion restricting member 40 tend to lift and open the distal end 42 of the elastomeric tube and to direct it back along the outer surface of the tube allowing the tube to at least partially evert and slide over itself and/or a portion of the elongated support member 20 as the filter deploys to a final state resembling FIG. 3.

Figure 4:
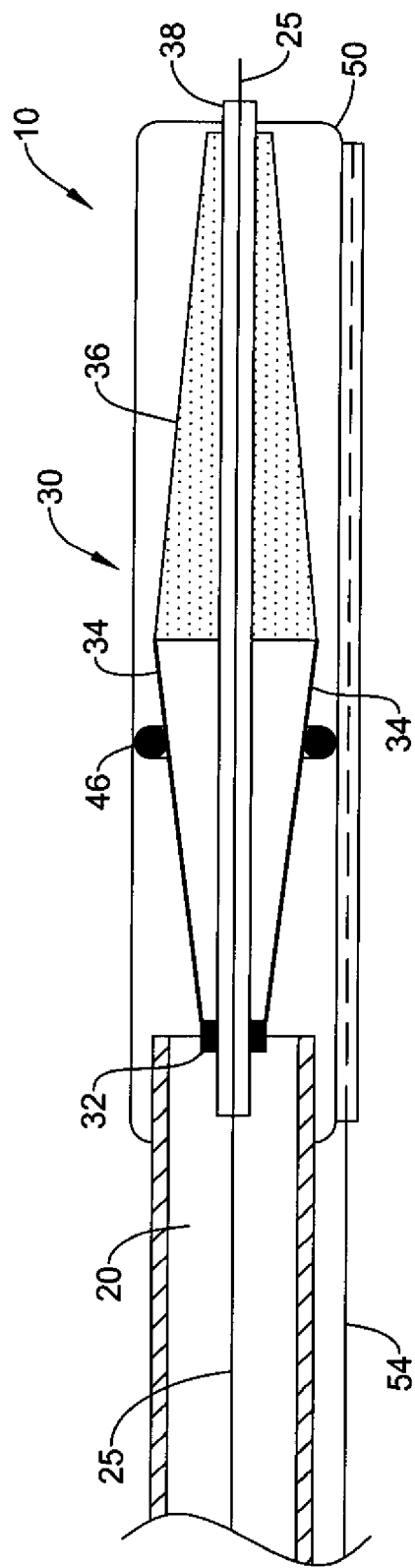
FIG. 4 is a cross-section view of an embolic filter in a collapsed state.
Figure 5:
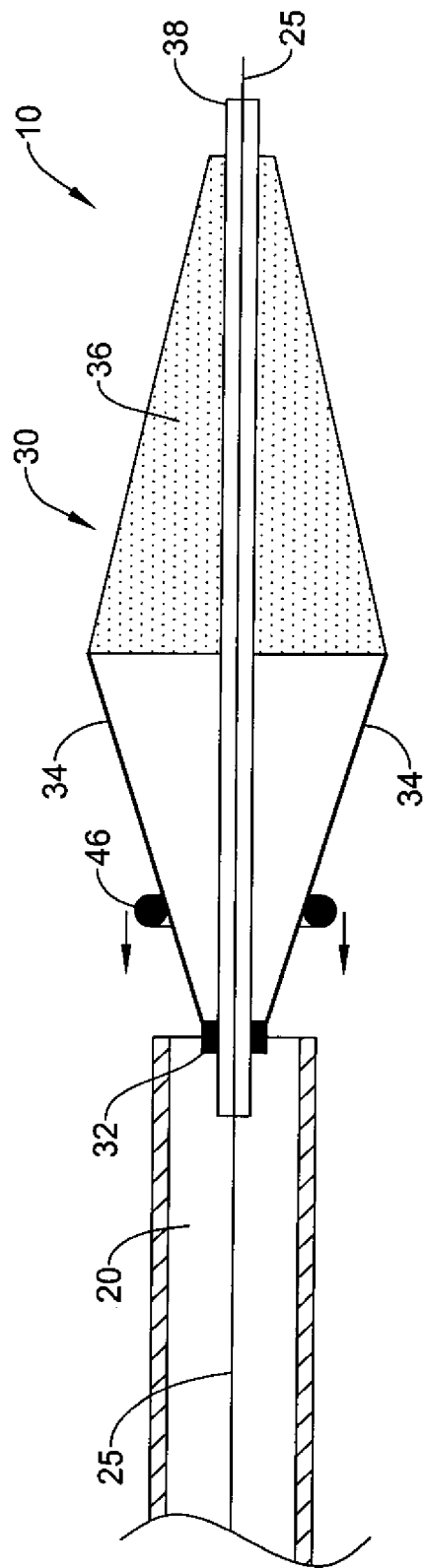
FIGS. 5 and 6 are cross-section views of the embolic filter of FIG. 4 as it deploys.
Figure 6:
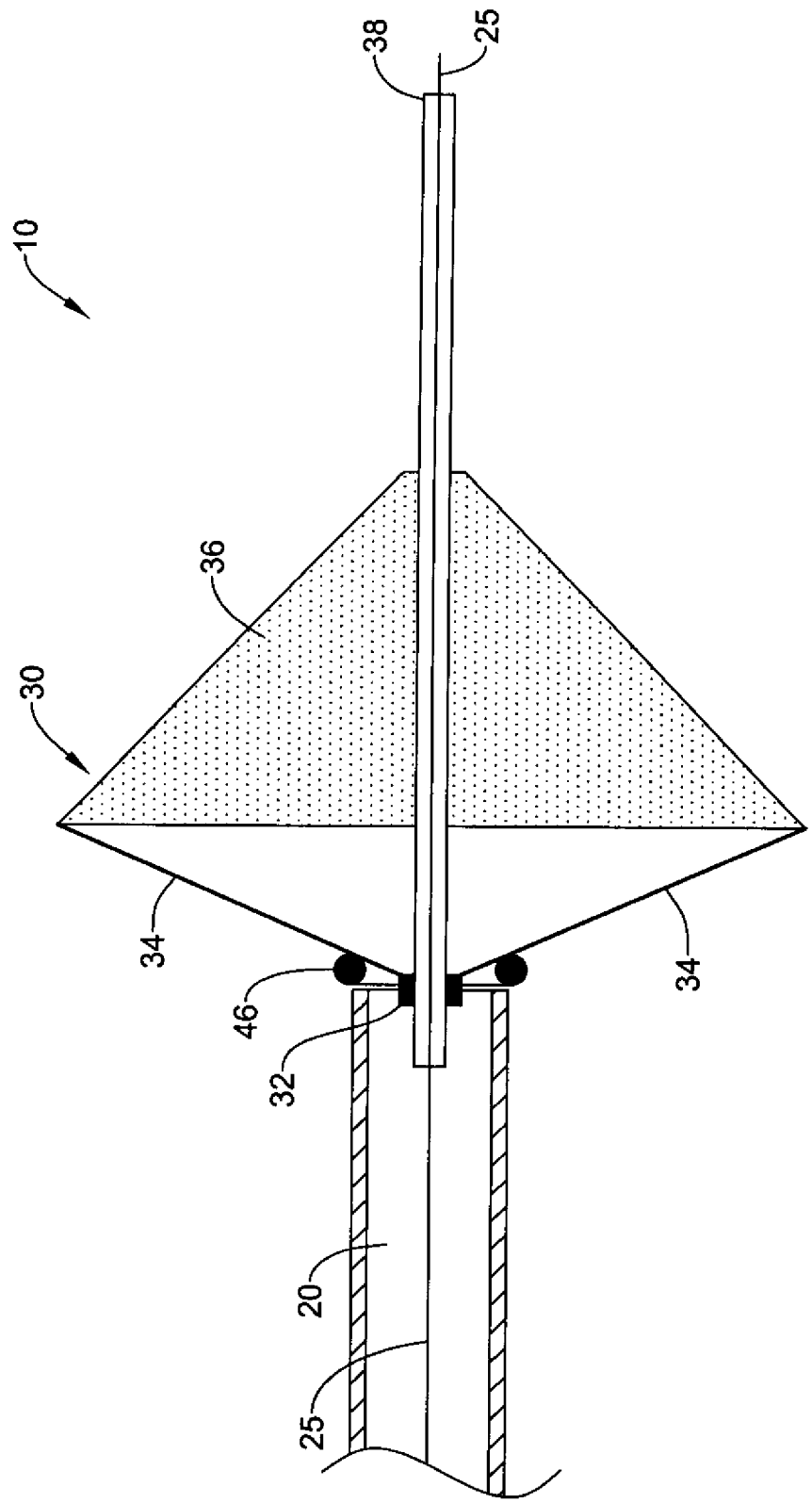
Figure 7:
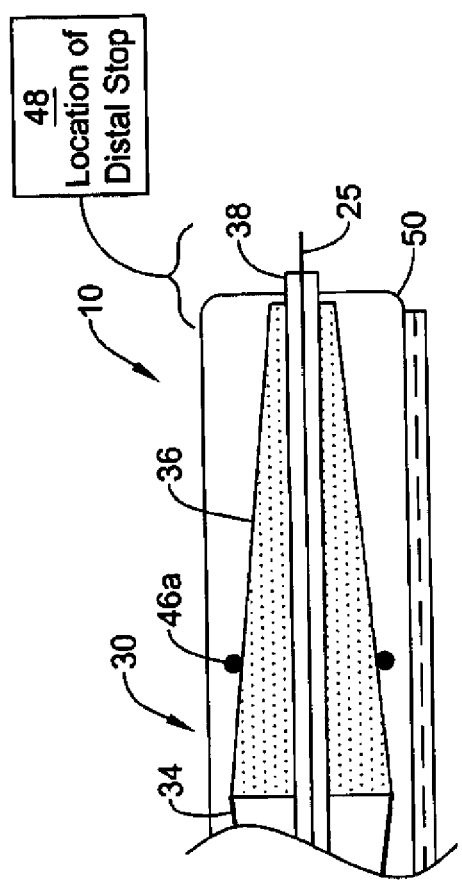
FIG. 7 is a detail of the distal portion of an embodiment of an embolic filter.

In the embodiments of FIGS. 4-6, the motion restricting tubular elastomeric element 40 has been replaced by a motion restricting ring 46. The ring 46 may be elastomeric, resembling an o-ring, in which case it may roll along the slopes of the expanding struts 34 under the influence of resolved forces as depicted in FIG. 5 or it may be substantially rigid providing that the coefficient of friction between the ring and the struts is low enough to allow the ring to slide along the struts as they expand. In either event, the ring reaches a position resembling that found in FIG. 6 as the filter is fully deployed.

The elongated support member 20, with which the filter 30 is associated, may be a hollow tube. In some embodiments, the support member may accommodate a guidewire 25, a spinner tube 38, or even the hub 32 of the filter within its lumen. In other embodiments, the lumen of the support member may be limited to the distal region of the support member and may optionally be provided with a lateral port. In yet other embodiments, the distal end of the elongated support member may form the hub of the filter. In yet other embodiments, the distal end of the elongated support member may be slit to form the outwardly biased struts. In these embodiments, as well as the more conventional hub and strut configurations, the elongated support member may be formed from a shape memory metal or polymer and the resulting struts 34 may be biased toward an expanded configuration by any of the methods known in the art. Some strut configurations may include both a distal hub (not shown) and a proximal hub 32 depending on the degree of filter membrane support desired. In addition to simple linear struts, the struts may be bifurcated, helical, or may be formed in any of a variety of configurations. The struts may be round, oval, rectangular, hexagonal, or combinations of these and other cross-sectional shapes. In addition to struts, the frame supporting the filter membrane, if it is present, may include rings, spars, tethers, and the like to further shape and reinforce the filter membrane 36.

Although the augmented constraint apparatus of the invention does not require that the filter to be constrained and delivered include a filter membrane 36, it is contemplated that many filters used with the apparatus will include one or more membrane elements rather than comprising only struts as might be found in a vena cava filter. When a filter membrane is present, it may be formed as a sheet or from a mesh. In some embodiments, it may be a molded article. It may include holes sized to pass common blood components such as red and white blood cells and yet retain emboli, thrombi, and other debris. The holes may be present in the material as formed, or they may be added later by laser drilling, punching, or the like. Some filter membranes may include skirts, bands, stiffeners, or other features which serve to improve the seal between the expanded filter and the lumen wall. The filter membrane 36 may be present in the form of a hemisphere, basket, cone, or frustum, as well as other shapes, at the discretion of the filter designer.

In some embodiments, the filter will be mounted on a spinner tube 38 which may, in turn, be mounted on a guidewire to provide limited translation as well as rotation to the filter. In such embodiments, it is common to employ proximal and or distal stops (not shown) to limit translation of the filter while still allowing for some incidental movement of the guidewire. The filter hub and/or the distal end of the filter or filter frame may be fixed to the spinner tube. In other embodiments, the filter may be mounted directly on the guidewire 25 or a catheter.

As discussed above, the motion restricting member may take any of a number of forms. In some embodiments, the motion restricting member may take the form of an elastomeric tube 40. The elastomeric tube may be positioned wholly over the struts, may abut the hub and extend over the struts, may be positioned over the hub and extend over the struts, or may be positioned over the distal end of the elongated support member and extend over the struts. The elastomeric tube may be stretched to fit over the struts and/or other structures. It may be swollen with solvent to facilitate initial stretching and subsequently dried to restore its constrictive force. Alternatively, it may be heat-shrunk in place. The inward force exerted by the motion restricting member is, in general, insufficient to prevent the outwardly biased struts 34 from self-expanding with out additional inward force. This force may be provided by the containment structure 50. As the struts separate following, for example, release of the containment structure by withdrawal of the activation element or ejection of the filter and motion restricting member from a delivery sheath, the forces on the motion restricting member tend to lift and open the distal end of the elastomeric tube while directing the distal end proximally along the outer surface of the tube allowing the tube to partially evert and slide over itself as the filter deploys to a final configuration. At an intermediate stage, an axial cross-section of the tube wall may resemble the letter "J" and later may resemble the letter "U". In some embodiments, the tube may incorporate beads, ridges or ribs which facilitate the transition between the extended tubular form and the partially everted "J" form and may also serve to maintain the axial alignment of the elastomeric tube as the struts move outward toward the deployed state. In other embodiments, auxiliary structures such as tethers, optionally linked to the activation member, may help to initiate eversion and may even be partially responsible for the rolling or peeling action. Similarly, structures on the struts may tend to engage the tube initially as the struts expand with a resulting partial eversion. In some embodiments, the elastomeric tubular member may be provided with a coating or other lubricant which reduces the friction between the inner and outer layers of the tube as the tube partially everts. In yet other embodiments, at least a portion of the tubular elastomeric member 40 may be disposed over the support member 20 and may remain stationary with respect to the support member. If the motion restricting member is allowed to move proximally until it is entirely over the support member, it may release the hub and any associated spinner tube to translate and/or rotate about a guidewire. In other embodiments, the elastomeric tube may be disposed over the hub in the deployed state and the support member may be withdrawn.

In other embodiments, the motion restricting member may take the form of an elastomeric o-ring 46 or a relatively rigid ring whose dimensions remain substantially unchanged as it slides along the struts 34. When such a ring is placed along the struts distal of the distal end of the end of the support member, it provides a degree of resistance to the expansion of the struts 34 which, in combination with a containment structure 50, prevents the expansion of the struts with attendant deployment of the filter. It will be appreciated that such a ring may have a form which is different from a circle with a circular cross-section if desired. As when the motion restricting member is an elastomeric ring, the inward force exerted by the ring generally will be insufficient to maintain the filter in a collapsed state when the containment structure 50 is released or removed. Once the containment structure is released or removed, the outward force will be capable of partially expanding the struts 34 such that they slope from a larger radial extension near the filter material toward the smaller hub portion and the ring may either roll or slide along the struts toward the hub thereby releasing the struts and the filter to expand within the lumen. As in the embodiments where the motion restricting member is a tubular elastomeric member, the initial proximal displacement of the ring may be assisted by an activation element 54, by structures associated with the struts, or by other means. Additionally, the struts 34 and/or the ring 46 may be provided with a coating or other lubricating material which reduces the rolling or sliding friction between the ring and the struts. As the ring moves proximally, it may come to rest on the hub 32, a spinner tube 38 if present, or the support member 20. In those embodiments in which the motion restricting member comes to rest on the support member after the filter is in the deployed state, the motion restricting member may be removed with the support member to free the guidewire for use to advance other devices to the site of the obstruction.

In addition to those embodiments in which at least a portion of the motion restricting member 46 moves proximally as the intraluminal filter 30 moves from a collapsed state to a deployed state, other embodiments in which a primary or a secondary motion restricting member 46a moves distally are also contemplated. For example, in those constructions in which the struts 34 extend the length of the filter assembly, a second motion restricting member 46a, such as a ring, may be placed near the distal end of the collapsed filter 30. As the filter 30 is released from the containment structure, the outward force of the struts 34 would then be partially redirected to roll or slide the motion restricting member 46a distally. In such embodiments, it may be desirable to provide a distal stop 48 or other mechanism (not shown) to retain the motion restricting member 46a once the filter 30 is deployed and to assist in its removal along with the filter later in the process.

As mentioned above, the containment structure 50 may one of those known in the art, including, but not limited to, those comprising a restraining member which wraps at least partially around the struts and or filter, said restraining member having two or more apertures through which an activation element 54 may be passed to complete the enclosing containment structure. In some embodiments, the restraining member will take the form of a strip or band with a plurality of apertures along opposed edges thereof. The activation element may then be passed alternately through the edges of first one and then the other edge in the manner of a sewn seam to create an enveloping tube having a diameter just large enough to accommodate the struts and or filter in the collapsed state of the filter assembly. In other embodiments, the apertures may take the form of short alternating tubes which are then linked in a manner of a common door hinge by the activation element which serves as the hinge pin in the containing configuration. In yet other configurations, the restraining member may take the form of a wire or string which zig-zags back and forth around the filter assembly and alternately wraps around the activation element to provide the desired restraint until the activation element is withdrawn. In yet other embodiments, the containment structure may be a simple sheath attached to the end of the activation element. In these and other embodiments, the containment structure may be somewhat reduced in bulk as at least a portion of the force necessary to maintain the outwardly biased struts in their collapsed state will be provided by the motion restricting member thereby leading to an overall reduced cross-section as the filter is advanced past an obstruction in the lumen. Unlike containment systems of the art, the combination of a motion restricting member and a containment structure tends to eliminate a bulge in the region of the struts associated with the greatest outward force thereby reducing the overall dimensions of the collapsed filter during delivery.

In other embodiments, the containment structure may resemble a conventional delivery sheath or catheter and the activation element may be a reduced diameter portion of the catheter or a retrieval wire affixed to the sheath. In certain embodiments in which the motion restricting member is a ring, the containment structure may include a ridge or groove (not shown) which engages the ring in a first position thereby preventing proximal motion of the ring until the containment structure is removed. In other embodiments, retrieval of the filter assembly after use may be assisted by providing a retrieval sheath which engages the ring as it is advanced over the struts distally causing the ring to roll or slide over the struts to once again collapse the struts in cooperation with additional restraining force supplied by the sheath. By employing a suitable retrieval sheath, a motion restricting member comprising an elastomeric tubular member may also be engaged and rolled back along the struts to assist in collapsing the filter following use.

The invention further relates to a method of containing and deploying a filter from within an augmented constraint apparatus as described above, the method comprising the steps of providing the filter 30, collapsing the filter, positioning a motion restricting member 40 to partially overcome the outward force of the outwardly biased struts 34 of the filter, supplying a containment structure 50 which provides the additional inward force necessary to maintain the filter in a collapsed state, positioning the filter and constraint apparatus in a lumen, and releasing or removing the containment structure 50 to allow the filter 30 to deploy within the lumen.

Although the illustrative examples described above relate to an embodiment in which the open mouth of the filter is directed proximally and away from the guidewire tip within the lumen, a reversal of the filter components is also contemplated to provide a filter in which the open mouth of the filter is directed distally and toward the guidewire tip. In such an embodiment, the descriptive terms "distal", "proximal", and their derivative forms may be exchanged as they relate to the filter and associated restraint components.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An augmented constraint apparatus for delivery and deployment of an intraluminal filter within a lumen comprising:

an elongated support member for an intraluminal filter, said support member having a proximal end, a distal end, and a shaft therebetween;
an intraluminal filter associated with the distal end of the support member, said filter comprising a plurality of outwardly biased struts, said filter having a collapsed state and a deployed state;
a motion restricting member having the form of a ring disposed about at least a portion of the outwardly biased struts of the filter in the collapsed state;
a containment structure having two or more apertures therein; and
an activation element having a first position and a second position, wherein in the first position, the activation element engages the two or more apertures of the containment structure and the containment structure encompasses at least a portion of the outwardly biased struts, further wherein in the second position, the activation element is disengaged from at least one of the apertures of the containment structure allowing the intraluminal filter to move from the collapsed state toward the deployed state thereby allowing the struts to at least partially expand moving at least a portion of the motion restricting member proximally from its first position to its second position as the filter deploys within the lumen; wherein the ring rolls along the outwardly biased struts of the filter as the filter moves from the collapsed state toward the deployed state.

2. The apparatus of claim 1, wherein the filter comprises a filter membrane.

3. The apparatus of claim 1, wherein the filter is mounted about a spinner tube disposed about a guidewire.

4. The apparatus of claim 1, further comprising a recovery sheath having a lumen therein, said lumen sized to at least partially contain the collapsed state of the filter, and having a distal opening sized to engage the motion restricting member and advance at least a portion of the motion restricting member over the plurality of outwardly biased struts as the recovery sheath is advanced distally.

5. The apparatus of claim 1, further comprising a second motion restricting member disposed about at least a second portion of the filter, wherein when the intraluminal filter moves from the collapsed state toward the deployed state, at least a portion of the second motion restricting member moves distally.

* * * * *